US012503662B1

United States Patent

(12) United States Patent
Karanjikar et al.

(10) Patent No.: US 12,503,662 B1
(45) Date of Patent: Dec. 23, 2025

(54) CYCLOOCTANE CONTAINING SEAL SWELLING COMPOSITIONS AND METHODS FOR USE OF SAME

(71) Applicant: CleanJoule, Inc., Salt Lake City, UT (US)

(72) Inventors: Mukund Karanjikar, Salt Lake City, UT (US); Robert Andrew Price, Salt Lake City, UT (US); Oyvind Hatlevik, Holladay, UT (US); Michael James Mella, South Jordan, UT (US)

(73) Assignee: CleanJoule, Inc., Salt Lake City, UT (US)

( * ) Notice: Subject to any disclaimer, the term of this patent is extended or adjusted under 35 U.S.C. 154(b) by 0 days.

(21) Appl. No.: 19/312,867

(22) Filed: Aug. 28, 2025

Related U.S. Application Data

(60) Provisional application No. 63/687,831, filed on Aug. 28, 2024.

(51) Int. Cl.
*C10L 10/00* (2006.01)
*C07C 13/26* (2006.01)
*C10L 1/16* (2006.01)

(52) U.S. Cl.
CPC .............. *C10L 10/00* (2013.01); *C07C 13/26* (2013.01); *C10L 1/1608* (2013.01); *C10L 2270/02* (2013.01)

(58) Field of Classification Search
None
See application file for complete search history.

(56) References Cited

U.S. PATENT DOCUMENTS

| | | | | |
|---|---|---|---|---|
| 5,906,662 | A | 5/1999 | McCombes | |
| 12,291,684 | B2 * | 5/2025 | Ramasamy | C10L 1/16 |
| 2001/0049427 | A1 * | 12/2001 | Atwood | C09K 3/1018 528/10 |
| 2009/0031614 | A1 * | 2/2009 | MacPherson | C10L 1/265 44/435 |
| 2012/0059205 | A1 * | 3/2012 | Rusek | C10G 45/32 585/302 |
| 2014/0250772 | A1 * | 9/2014 | Woolard | C10L 10/00 44/448 |
| 2015/0259619 | A1 | 9/2015 | Albuzat et al. | |
| 2015/0291906 | A1 | 10/2015 | DeSantis et al. | |
| 2017/0101594 | A1 * | 4/2017 | Stevenson | C10L 1/2383 |
| 2018/0016509 | A1 * | 1/2018 | D'Acosta | C10L 10/14 |
| 2019/0203143 | A1 | 7/2019 | Hussain et al. | |
| 2019/0292478 | A1 | 9/2019 | Hussain et al. | |
| 2025/0207054 | A1 * | 6/2025 | Labb | C10M 129/54 |

* cited by examiner

*Primary Examiner* — Ali Z Fadhel
(74) *Attorney, Agent, or Firm* — Caldwell Intellectual Property Law

(57) ABSTRACT

A method for use of seal swelling compositions includes receiving a composition including one or more compounds according to formula (I), wherein each R independently represents a hydrogen atom or an alkyl group; and applying the composition to a first number of elastomeric seals to facilitate swelling of the first number of elastomeric seals.

20 Claims, 6 Drawing Sheets

(1s,4s)-1-isopropyl-4-methylcyclohexane (1S,3R)-1-isopropyl-3-methylcyclohexane (1s,4s)-1-ethyl-1,4-dimethylcyclohexane (1S,3S)-1-isopropyl-3-methylcyclohexane (1r,4r)-1-ethyl-1,4-dimethylcyclohexane (1R,3S)-1-ethyl-1,3-dimethylcyclohexane (1r,4r)-1-isopropyl-4-methylcyclohexane (1R,3R)-1-ethyl-1,3-dimethylcyclohexane

CYCLOOCTANE CONTAINING SEAL SWELLING COMPOSITIONS AND METHODS FOR USE OF SAME

CROSS-REFERENCE TO RELATED APPLICATIONS

This application claims the benefit of priority of U.S. Provisional Patent Application Ser. No. 63/687,831, filed on Aug. 28, 2024, and titled "CYCLOOCTANE CONTAINING SEAL SWELLING COMPOSITIONS AND METHODS FOR USE OF SAME," which is incorporated by reference herein in its entirety.

FIELD OF THE INVENTION

The present invention generally relates to the field of seal swelling compositions. In particular, the present invention is directed to cyclooctane containing seal swelling composition and methods for use of same.

BACKGROUND

Elastomeric seals may be used in a variety of different environments. In some applications for example, elastomeric seals may be used in the interconnection of components in a fluid fuel system and/or an internal combustion engine to prevent fluid leakage at the interconnection of components. In order to provide adequate sealing at the interconnection of components, some elastomeric materials may need to undergo some degree of swelling in order to increase their size and/or volume and make sufficient contact with adjacent components. The increase in size and/or volume may, for example, account for machining tolerances at the interconnection of the components and/or an area in which the seal itself is positioned. In some forms, the elastomeric seals may be designed to swell due to the presence of a fluid in the environment in which they are positioned.

SUMMARY OF THE DISCLOSURE

In an aspect, a method for use of seal swelling compositions includes receiving a composition including one or more compounds according to formula (I)

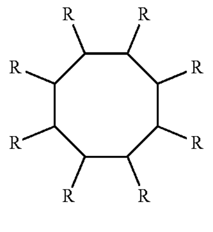

wherein each R independently represents a hydrogen atom or an alkyl group; and applying the composition to a first number of elastomeric seals to facilitate swelling of the first number of elastomeric seals.

In another aspect, an elastomeric seal includes a body configured to expand from a first configuration having a first volume to a second configuration having a second volume larger than the first volume in response to exposure to a composition including one or more compounds according to formula (I)

(I)

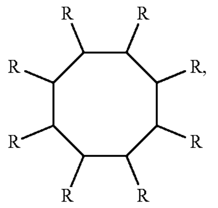

wherein each R independently represents a hydrogen atom or an alkyl group.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1A:
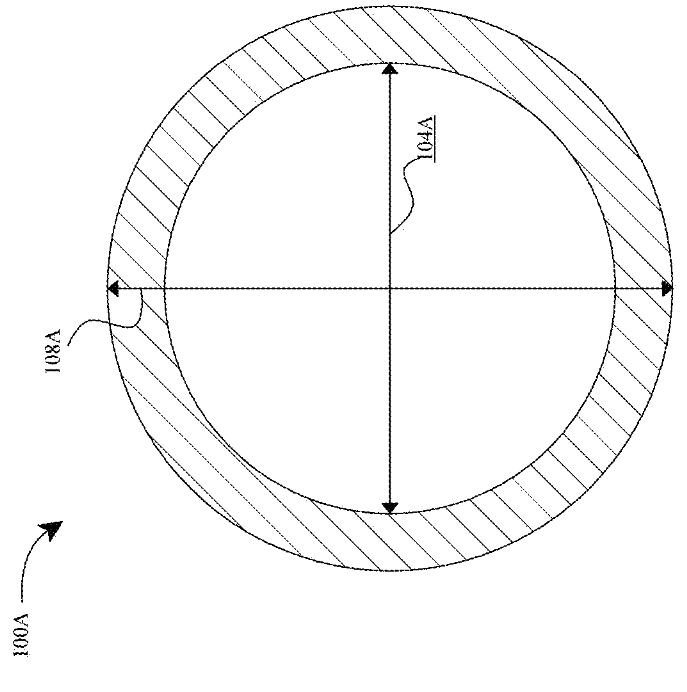
FIGS. 1A-B are schematic illustrations of an elastomeric seal.

The drawings are not necessarily to scale and may be illustrated by phantom lines, diagrammatic representations, and fragmentary views. In certain instances, details that are not necessary for an understanding of the embodiments or that render other details difficult to perceive may have been omitted. Like reference symbols in the various drawings indicate like elements.

DETAILED DESCRIPTION

Aspects of the present disclosure may be related to compositions for swelling an elastomeric seal and to uses of the same. Aspects of the present disclosure may be used to compositions which include one or more cyclooctane compounds and the use thereof to induce swelling of an elastomeric seal when the elastomeric seal is exposed to the composition. Aspects of the present disclosure may be used to reduce the dependence on fossil fuels and mitigate the negative environmental impacts thereof. Exemplary embodiments illustrating aspects of the present disclosure are described below in the context of several specific examples.

In an embodiment, a composition includes one or more compounds according to formula (I)

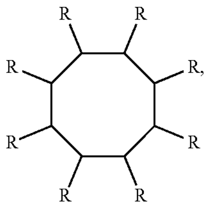

(I)

where each R independently represents a hydrogen atom or an or an alkyl group.

Regarding one or more compounds of formula (I), a non-limiting method of preparation includes reacting a conjugated diene, or a mixture of conjugated dienes, with a catalyst selected from the group consisting of: a low-valent iron catalyst stabilized with a pyridineimine ligand; an iron precatalyst coordinated to a pyridineimine ligand and activated with a reducing agent; a low oxidation state iron complex stabilized with a pyridineimine ligand and a coordinating ligand; and combinations thereof, thereby forming a substituted cyclooctadiene. The reaction is carried out under an inert atmosphere, optionally using the diene as both solvent and reactant, at a temperature ranging from about −80° C. to about 100° C., for a duration of about 1 to 48 hours. In various embodiments, the molar ratio of diene to catalyst ranges from about 100:1 to about 1,000,000:1, and is approximately 4,000:1 in a specific example. More particular but non-limiting compounds according to formula (I) which may be included in the compositions described herein, either alone or in some combination, include the following:

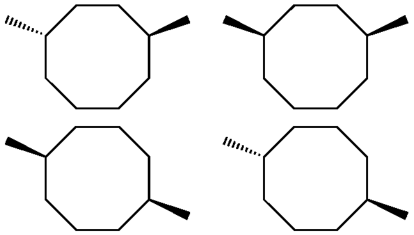

These compounds may include (1R,4S)-1,4-dimethylcyclooctane, (1S,4S)-1,4-dimethylcyclooctane, (1s,5s)-1,5-dimethylcyclooctane, (1r,5r)-1,5-dimethylcyclooctane. “DMCO” may be used herein to refer to any of these compounds individually or to any combination thereof. These compounds may be prepared in accordance with the following reaction scheme:

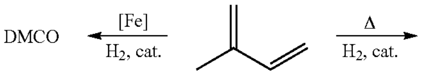

isoprene

-continued

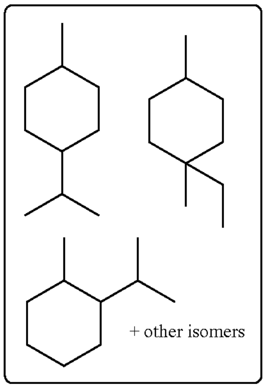

HID

In an embodiment, a method may be provided for producing a 1,4-dimethylcyclooctane (DMCO) from isoprene through an iron-catalyzed hydrogenation process. In this reaction scheme, isoprene may undergo dimerization and subsequent hydrogenation in the presence of an iron-based catalyst under hydrogenation conditions to form DMCO. In an embodiment, isoprene starting material may include a mixture of isoprene monomers obtained from renewable or petrochemical feedstocks. During the hydrogenation step, a catalyst comprising iron, optionally with supporting ligands, may be exposed to hydrogen to promote the conversion of isoprene to DMCO with controlled selectivity. As a side product, a hydrogenated isoprene dimers (HID) fraction may be formed, comprising a range of saturated C10 cycloalkane isomers. In an embodiment, HID fraction may include 1-isopropyl-4-methylcyclohexane, 1-ethyl-1,4-dimethylcyclohexane, 1-isopropyl-2-methylcyclohexane and other branched cycloalkanes. In this reaction scheme, HID is representative of hydrogenated isoprene dimers (HID) which are also a product of the reaction scheme, and HID may also include about 10% to about 15% by weight of DMCO. HID may additionally or alternatively be representative of compounds having one of the following structures:

1

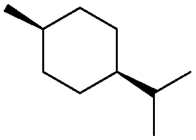

2

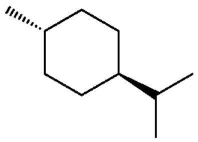

3

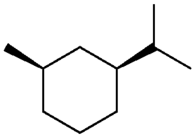

-continued

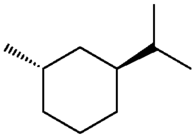

4

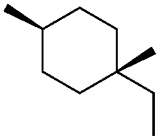

5

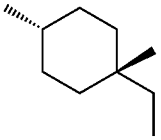

6

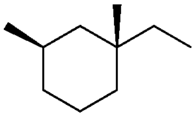

7

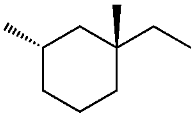

8

In one or more embodiment, HIDs may include (1s,4s)-1-isopropyl-4-methylcyclohexane (1), (1s,4s)-1-ethyl-1,4-dimethylcyclohexane (2), (1S,3R)-1-isopropyl-3-methylcyclohexane (3), (1S,3S)-1-isopropyl-3-methylcyclohexane (4), (1r,4r)-1-ethyl-1,4-dimethylcyclohexane (5), (1r,4r)-1-isopropyl-4-methylcyclohexane (6), (1R,3S)-1-ethyl-1,3-dimethylcyclohexane (7), (1R,3R)-1-ethyl-1,3-dimethylcyclohexane (8). In some forms, the compositions described herein may include one or more of the compounds represented by HID.

In one or more embodiments, one or more composition may include one or more n-alkanes, one or more iso-alkanes, or a mixture of one or more n-alkanes and one or more iso-alkanes. When a mixture of one or more n-alkanes and one or more iso-alkanes is included, the one or more n-alkanes and one or more iso-alkanes may include those found in hydrogen processed esters and fatty acid compositions known as hydroprocessed esters and fatty acids (HEFA) or HEFA-Jet. In one or more embodiments, various embodiments of HEFA may include HEFA-SPK (Hydroprocessed Esters and Fatty Acids-Synthetic Paraffinic Kerosene), and HVO (Hydrotreated Vegetable Oil). However, the inclusion of additional and/or alternative n-alkanes and/or iso-alkanes may also be possible and contemplated. In some forms, the n-alkane may include n-decane, the iso-alkane may include iso-decane, and the mixture may include n-decane and iso-decane not limiting examples of which include 2-methyl nonane, 3-methyl nonane, 4-methyl nonane, 2,2-dimethyl octane, 3,3-dimethyl octane, 4,4-dimethyl octane, 2,3-dimethyl octane, 2,4-dimethyl octane, 2,5-dimethyl octane, 2,6-dimethyl octane, 2,7-dimethyl octane, 3,4-dimethyl octane, 3,5-dimethyl octane, 3,6-dimethyl octane, 2,2,3-trimethyl heptane, 2,2,4-trimethyl heptane, 2,2,5-trimethyl heptane, 2,2,6-trimethyl heptane, 2,3,3-trimethyl heptane, 2,3,4-trimethyl heptane, 2,3,5-trimethyl heptane, 2,3,6-trimethyl heptane, 3,3,4-trimethyl heptane, 2,2,3,3-tetramethyl hexane, 2,2,4,4-tetramethyl hexane, 2,2,5,5-tetramethyl hexane, 2,3,3,4-tetramethyl hexane, 2,3,3,5-tetramethyl hexane, 2,3,4,5-tetramethyl hexane, 2,2,3,3,4-pentamethyl pentane and 2,2,3,4,4-pentamethyl pentane.

In one or more embodiments, an amount of one or more compounds according to formula (I) and at least one n-alkane, at least one iso-alkane or the mixture thereof may be varied depending on various properties of the one or more compounds according to formula (I) and at least one n-alkane, at least one iso-alkane or a mixture thereof as necessary to provide a composition with desired properties or characteristics such as density or derived cetane number.

In one or more embodiments, one or more compounds according to formula (I) may be present at about 1% to about 100% by weight based on a total weight of a composition. However, other variations may be contemplated and possible. For example and without limitation, one or more compounds according to formula (I) may be present at about 2% to about 99% by weight based on a total weight of the composition, at about 5% to about 95% by weight based on a total weight of the composition, at about 10% to about 90% by weight based on a total weight of a total weight of the composition, at about 20% to about 85% by weight based on a total weight of the composition, at about 25% to about 80% by weight based on a total weight of the composition, at about 30% to about 70% by weight based on a total weight of the composition, at about 40% to about 60% by weight based on a total weight of the composition, at about 50% to about 99% by weight based on a total weight of the composition, at about 33% to about 66% by weight based on a total weight of the composition, or in any range defined by one or more of these values.

In one or more embodiments, compositions including one or more compounds according to formula (I) as described herein may induce swelling of an elastomeric seal when the elastomeric seal is exposed to the composition. In one or more embodiments, elastomeric seal may include but are not limited to nitrile rubber (NBR), fluorosilicone rubber, fluoroelastomers, acrylate-based elastomers (O-rings), additive-manufactured (AM) elastomers (acrylate/dimethacrylate).

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

It is understood that the acts described below are meant as a general overview and demonstration of an exemplary method, and that the method may include different and/or additional acts as described herein or otherwise.

While the present invention will be described as having particular configurations disclosed herein, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

It is to be understood that any aspect and/or element of any embodiment of the method(s) described herein or otherwise may be combined in any way to form additional embodiments of the method(s) all of which are within the scope of the method(s).

Where a process is described herein, those of ordinary skill in the art will appreciate that the process may operate without any user intervention. In another embodiment, the process includes some human intervention (for example, a step is performed by or with the assistance of a human).

For the purposes of this disclosure, including the claims, the phrase "at least some" means "one or more" and includes the case of only one. Thus, for example, the phrase "at least some ABCs" means "one or more ABCs" and includes the case of only one ABC.

For the purposes of this disclosure, including the claims, the term "at least one" should be understood as meaning "one or more" and therefore includes both embodiments that include one or multiple components. Furthermore, dependent claims that refer to independent claims that describe features with "at least one" have the same meaning, both when the feature is referred to as "the" and "the at least one."

For the purposes of this disclosure, the term "portion" means some or all. Therefore, for example, "A portion of X" may include some of "X" or all of "X." In the context of a conversation, the term "portion" means some or all of the conversation.

For the purposes of this disclosure, including the claims, the phrase "using" means "using at least" and is not exclusive. Thus, for example, the phrase "using X" means "using at least X." Unless specifically stated by use of the word "only," the phrase "using X" does not mean "using only X."

For the purposes of this disclosure, including the claims, the phrase "based on" means "based in part on" or "based, at least in part, on" and is not exclusive. Thus, for example, the phrase "based on factor X" means "based in part on factor X" or "based, at least in part, on factor X." Unless specifically stated by use of the word "only," the phrase "based on X" does not mean "based only on X."

In general, for the purposes of this disclosure, including the claims, unless the word "only" is specifically used in a phrase, it should not be read into that phrase.

For the purposes of this disclosure, including the claims, the phrase "distinct" means "at least partially distinct." Unless specifically stated, distinct does not mean fully distinct. Thus, for example, the phrase "X is distinct from Y" means that "X is at least partially distinct from Y" and does not mean that "X is fully distinct from Y." Thus, for the purposes of this disclosure, including the claims, the phrase "X is distinct from Y" means that X differs from Y in at least some way.

It should be appreciated that the words "first," "second," and so on, in the description and claims, are used to distinguish or identify, and not to show a serial or numerical limitation.

Similarly, letter labels (for example, "(A)," "(B)," "(C)," and so on, or "(a)," "(b)," and so on) and/or numbers (for example, "(i)," "(ii)," and so on) are used to assist in readability and to help distinguish or identify, and are not intended to be otherwise limiting or to impose or imply any serial or numerical limitations or orderings. Similarly, words such as "particular," "specific," "certain," and "given," in the description and claims, if used, are to distinguish or identify, and are not intended to be otherwise limiting.

For the purposes of this disclosure, including the claims, the terms "multiple" and "plurality" mean "two or more," and include the case of "two." Thus, for example, the phrase "multiple ABCs" means "two or more ABCs" and includes "two ABCs." Similarly, for example, the phrase "multiple PQRs" means "two or more PQRs" and includes "two PQRs."

The present invention also covers the exact terms, features, values, and ranges, etc., in case these terms, features, values, and ranges, etc., are used in conjunction with terms such as "about," "around," "generally," "substantially," "essentially," "at least," etc. Thus, for example, "about 3" or "approximately 3" shall also cover exactly 3, and "substantially constant" shall also cover exactly constant.

For the purposes of this disclosure, unless stated otherwise, the terms "about" or "approximately" refer to a value that is within 10% above or below the value being described.

For the purposes of this disclosure, including the claims, singular forms of terms are to be construed as also including the plural form and vice versa, unless the context indicates otherwise. Thus, it should be noted that for the purposes of this disclosure, the singular forms "a," "an," and "the" include plural references unless the context clearly dictates otherwise. In other words, terms such as "a," "an," and "the" are not intended to refer to only a singular entity but include the general class of which a specific example may be used for illustration.

Throughout the description and claims, the terms "comprise," "including," "having," "contain," and their variations should be understood as meaning "including but not limited to" and are not intended to exclude other components unless specifically so stated.

It will be appreciated that variations to the embodiments of the invention can be made while still falling within the scope of the invention. Alternative features serving the same, equivalent, or similar purpose can replace features disclosed in the specification, unless stated otherwise. Thus, unless stated otherwise, each feature disclosed represents one example of a generic series of equivalent or similar features.

Use of exemplary language, such as "for instance," "such as," "for example" ("e.g.,") and the like, is merely intended to better illustrate the invention and does not indicate a limitation on the scope of the invention unless specifically so claimed.

While the invention has been described in connection with what is presently considered to be the most practical and embodiments thereof are further described in the examples below, it is to be understood that the invention is not to be limited to the disclosed embodiment, but on the contrary, is intended to cover various modifications and equivalent arrangements included within the spirit and scope of the appended claims.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, and/or components have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Definitions

Definitions of specific functional groups and chemical terms are described in more detail below. For purposes of this invention, the chemical elements are identified in accordance with the Periodic Table of the Elements, Chemical Abstracts Service (CAS) version of the periodic table of the elements, Handbook of Chemistry and Physics, 106th Ed., inside cover, and specific functional groups are generally defined as described therein. Additionally, general principles of organic chemistry, as well as specific functional moieties and reactivity, are described in Organic Chemistry, Thomas Sorrell, 2nd Edition, University Science Books, 2006; Smith, March's Advanced Organic Chemistry: Reactions, Mechanisms, and Structure, 9th Edition, Wiley, 2025; Larock, Comprehensive Organic Transformations, 3rd Edition, Wiley, 2018; Carruthers and Coldham, Modern Methods of Organic Synthesis, 4th Edition, Cambridge University Press, Cambridge, 2004.

The term, "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms (C1-20 alkyl). In another embodiment the alkyl group contains 1-15 carbon atoms (C1-15 alkyl), in another embodiment the alkyl group contains 1-10 carbon atoms (C1-10 alkyl). In another embodiment the alkyl group contains 1-8 carbon atoms (C1-8 alkyl). In another embodiment the alkyl group contains 1-6 carbon atoms (C1-6 alkyl). In another embodiment the alkyl group contains 1-5 carbon atoms (C1-5 alkyl). In another embodiment the alkyl group contains 1-4 carbon atoms (C1-4 alkyl). In another embodiment the alkyl group contains 1-3 carbon atoms (C1-3 alkyl). In another embodiment, the alkyl group contains 1-2 carbon atoms (C1-2 alkyl), with examples of alkyl radicals including, but not limited to, methyl, ethyl, n-propyl, isopropyl, n-butyl, sec-butyl, iso-butyl, tert-butyl, n-pentyl, neopentyl, n-hexyl, sec-hexyl, n-heptyl, n-octyl, n-decyl, n-undecyl, dodecyl, and the like, which may bear one or more substituents, and alkyl group substituents include, but are not limited to, any of the substituents described herein that result in the formation of a stable moiety. The term "alkylene," as used herein, refers to a biradical derived from an alkyl group as defined herein by removal of two hydrogen atoms. An alkylene group may be cyclic or acyclic. It may also be branched or unbranched. An alkylene group may be substituted or unsubstituted. Substituents on the alkylene group may include, but are not limited to, any of the substituents described herein that result in the formation of a stable moiety.

The term, "aryl," as used herein, refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic C4-C20 aromatic ring system having one, two, or three aromatic rings which include, but are not limited to, phenyl, biphenyl, naphthyl, and the like, which may bear one or more substituents. Aryl substituents include, but are not limited to, any of the substituents described herein, that result in the formation of a stable moiety.

The term, "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

The term, "heteroaryl," as used herein, refers to an aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety.

The term, "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, which result in the formation of a stable moiety.

At a high level, aspects of the present disclosure are directed to cyclooctane containing seal swelling composition and methods for use of same.

Aspects of the present disclosure can be used as a method for use of seal swelling compositions including one or more compounds according to formula (I), wherein each R independently represents a hydrogen atom or an alkyl group; and applying the composition to a first number of elastomeric seals to facilitate swelling of the first number of elastomeric seals.

Aspects of the present disclosure can be used to an elastomeric seal includes a body configured to expand from a first configuration having a first volume to a second configuration having a second volume larger than the first volume in response to exposure to a composition including one or more compounds according to formula (I), wherein each R independently represents a hydrogen atom or an alkyl group.

Exemplary embodiments illustrating aspects of the present disclosure are described below in the context of several specific examples.

Figure 1B:
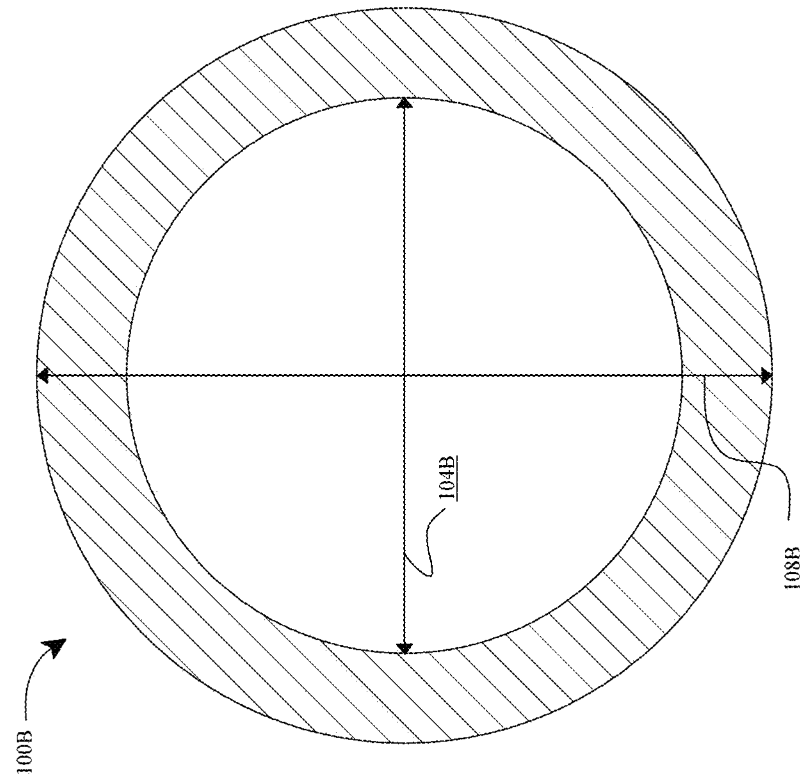

Referring now to FIGS. 1A-B, exemplary embodiments of elastomeric seals 100A-B are illustrated. In one or more embodiments, elastomeric seals 100A-B may experience swelling when exposed to certain fluids. An "elastomeric seal," as used in this disclosure, is a component made from a flexible, rubber-like polymer. In one or more embodiments, elastomeric seal may include O-ring and gasket. In one or more embodiments, elastomeric seal may be configured to undergo significant elastic deformation and return to its original shape. In one or more embodiments, elastomeric seal may be configured to form tight, leak-proof barriers between joined surfaces. In one or more embodiments, elastomeric seal may be configured to prevent an escape of fluids (liquids or gases) between joined parts in machinery, tanks, pipelines, pump bodies, valve bodies, injectors, fuel system assemblies, refueling equipment, aircraft engine, heavy vehicle engines, and fuel storage depots. In one or more embodiments, elastomeric seal may be configured to be compressed between two surfaces and its elasticity and swelling behaviors allow it to maintain contact pressure and fill any micro-imperfections, thereby ensuring a continuous barrier. In one or more embodiments, an elastomeric seal may be exposed to hydrocarbon fuels including, but not limited to, petroleum diesel, jet fuel, and gasoline, as well as to blends including, but not limited to, Sustainable Aviation Fuel (SAF), Gas-to-Liquids (GTL) fuels, and Fatty Acid Methyl Ester (FAME) blends, which may be used in various transportation and energy applications. In one or more embodiments, elastomeric seal may be configured to prevent environmental leaks and operational hazard leaks. In one or more embodiments, elastomeric seal may be configured to prevent vapor ingress or escape. In one or more embodiments, elastomeric seal may be configured to swell to a controlled degree in contact with fuel. In one or more embodiments, fuel additives may be added to interact with an elastomeric seal to induce sufficient swell to ensure sealing performance over time. "Swelling," as used in this disclosure, is a process by which an elastomer absorbs a liquid that results in an increase in the elastomer's volume or mass. In one or more embodiments, swelling may happen in a fuel environment. In one or more embodiments, at a molecular level, swelling may include liquid penetrates and physically expands a polymer network, causing a material to become larger and sometimes softer. In one or more embodiments, swelling may be deliberately controlled to maintain pressure between a seal and mating hardware as a material undergoes compression and mechanical aging. In one or more embodiments, elastomers in fuel systems may be subjected to long-term compression and repeat fuel exposure, wherein controlled swelling may help elastomer seals to recover dimensional compliance lost due to compression-set, thus maintaining a tight seal for an operational lifetime. In one or more embodiments, degree of swelling may be closely tied to chemical similarity between fuel additives and elastomer seal.

Referring now to FIGS. 1A-B, elastomeric seals 100A-B are illustrated. In one or more embodiments, a composition including one or more compounds according to formula (I) as described herein may induce swelling of elastomeric seals 100A-B when elastomeric seals are exposed to the composition. In one or more embodiments, a composition includes formula (I)

(I)

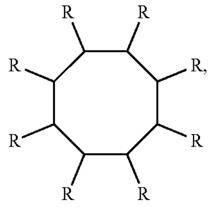

where each R independently represents a hydrogen atom or an or an alkyl group. In one or more embodiments, formula (I) may include (1R,4S)-1,4-dimethylcyclooctane, (1S,4S)-1,4-dimethylcyclooctane, (1s,5s)-1,5-dimethylcyclooctane, (1r,5r)-1,5-dimethylcyclooctane.

With continued reference to FIGS. 1A-B, in one or more embodiments, one or more compounds may include HIDs.

In one or more embodiment, HIDs may include (1s,4s)-1-isopropyl-4-methylcyclohexane (1), (1s,4s)-1-ethyl-1,4-dimethylcyclohexane (2), (1S,3R)-1-isopropyl-3-methylcyclohexane (3), (1S,3S)-1-isopropyl-3-methylcyclohexane (4), (1r,4r)-1-ethyl-1,4-dimethylcyclohexane (5), (1r,4r)-1-isopropyl-4-methylcyclohexane (6), (1R,3S)-1-ethyl-1,3-dimethylcyclohexane (7), (1R,3R)-1-ethyl-1,3-dimethylcyclohexane (8). In some forms, the compositions described herein may include one or more of the compounds represented by HID.

With continued reference to FIGS. 1A-B, in one or more embodiments, one or more compounds may include one or more n-alkanes, one or more iso-alkanes, or a mixture of one or more n-alkanes and one or more iso-alkanes. When a mixture of one or more n-alkanes and one or more iso-alkanes is included, the one or more n-alkanes and one or more iso-alkanes may include those found in hydrogen processed esters and fatty acid compositions known as hydroprocessed esters and fatty acids (HEFA) or HEFA-Jet. In one or more embodiments, various embodiments of HEFA may include HEFA-SPK (Hydroprocessed Esters and Fatty Acids—Synthetic Paraffinic Kerosene), and HVO (Hydrotreated Vegetable Oil). However, the inclusion of additional and/or alternative n-alkanes and/or iso-alkanes may also be possible and contemplated. In some forms, the n-alkane may include n-decane, the iso-alkane may include iso-decane, and the mixture may include n-decane and iso-decane not limiting examples of which include 2-methyl nonane, 3-methyl nonane, 4-methyl nonane, 2,2-dimethyl octane, 3,3-dimethyl octane, 4,4-dimethyl octane, 2,3-dimethyl octane, 2,4-dimethyl octane, 2,5-dimethyl octane, 2,6-dimethyl octane, 2,7-dimethyl octane, 3,4-dimethyl octane, 3,5-dimethyl octane, 3,6-dimethyl octane, 2,2,3-trimethyl heptane, 2,2,4-trimethyl heptane, 2,2,5-trimethyl heptane, 2,2,6-trimethyl heptane, 2,3,3-trimethyl heptane, 2,3,4-trimethyl heptane, 2,3,5-trimethyl heptane, 2,3,6-trimethyl heptane, 3,3,4-trimethyl heptane, 2,2,3,3-tetramethyl hexane, 2,2,4,4-tetramethyl hexane, 2,2,5,5-tetramethyl hexane, 2,3,3,4-tetramethyl hexane, 2,3,3,5-tetramethyl hexane, 2,3,4,5-tetramethyl hexane, 2,2,3,3,4-pentamethyl pentane and 2,2,3,4,4-pentamethyl pentane.

With continued reference to FIGS. 1A-B, in one or more embodiments, one or more compounds may be present at about 1% to about 100% by weight based on a total weight of a composition. However, other variations may be contemplated and possible. For example and without limitation, one or more compounds according to formula (I) may be present at about 2% to about 99% by weight based on a total weight of the composition, at about 5% to about 95% by weight based on a total weight of the composition, at about 10% to about 90% by weight based on a total weight of a total weight of the composition, at about 20% to about 85% by weight based on a total weight of the composition, at about 25% to about 80% by weight based on a total weight of the composition, at about 30% to about 70% by weight based on a total weight of the composition, at about 40% to about 60% by weight based on a total weight of the composition, at about 50% to about 99% by weight based on a total weight of the composition, at about 33% to about 66% by weight based on a total weight of the composition, or in any range defined by one or more of these values.

With continued reference to FIGS. 1A-B, in one or more embodiments, one or more compounds may be free of any aryl containing, arylene containing, heteroaryl containing, and heteroarylene containing compounds. For example, and without limitation, aryl may include phenyl, biphenyl, naphthyl, and the like. For example and without limitation, heteroaryl may include pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like.

With continued reference to FIGS. 1A-B, in one or more embodiments, one or more compounds may be free of any petroleum-based compounds. "Petroleum-based compounds," as used in this disclosure, are substances that are associated with petroleum production and are derived from the processing of crude oil or natural gas, rather than produced through chemical synthesis in a laboratory setting. In one or more embodiments, petroleum-based compounds may include, but are not limited to, alkanes (e.g., hexane, heptane, octane, decane), cycloalkanes (e.g., cyclohexane, methylcyclohexane), aromatic hydrocarbons (e.g., benzene, toluene, xylene, ethylbenzene, naphthalene), polycyclic aromatics (e.g., anthracene, phenanthrene), petroleum distillates (e.g., kerosene, diesel, naphtha, jet fuel), lubricating oils, paraffin wax, petroleum waxes, asphalt, and liquefied petroleum gases (e.g., propane and butane). In one or more embodiments, petroleum-based compounds may include all hydrocarbons that are extracted from or refined from petroleum or petroleum fractions.

With continued reference to FIGS. 1A-B, in one or more embodiments, one or more compounds may include petroleum-based compounds. In one or more embodiments, one or more compounds may be blended with petroleum-based fuels, including but are not limited to jet fuel, diesel, or gasoline, to form blended fuels suitable for aviation and other transportation applications. In one or more embodiments, blending may be necessary to ensure compatibility with existing fuel systems, particularly to maintain elastomeric seal swelling performance and avoid seal shrinkage, which may occur when neat alternative fuels lack aromatic or cycloalkane content. For example, and without limitation, petroleum-based aromatics in conventional jet fuel may contribute to the swelling of nitrile rubber or fluorosilicone elastomeric seals, thereby preserving sealing function and preventing fuel leakage. In one or more embodiments, fuels produced through pathways such as Gas-to-Liquids (GTL) or Hydroprocessed Esters and Fatty Acids (HEFA) may have low aromatic content, which may lead to insufficient swelling of elastomeric seals. In one or more embodiments, one or more compounds according to the present disclosure may be blended with petroleum-based fuels to achieve suitable aromatics concentration, fuel density, and seal swell behavior for safe and reliable operation in aviation or other transport engines. In one or more embodiments, blending one or more compounds with petroleum-based compounds may provide a pathway for reducing fossil carbon emissions while maintaining compatibility with existing infrastructure and engine materials.

With continued reference to FIGS. 1A-B, in one or more embodiments, one or more compounds may be mixed with one or more fuel compositions selected from the group consisting of synthetic paraffinic kerosene (SPK), Jet-A fuel, HEFA, HEFA-Jet and L-Jet. In one or more embodiments, one or more compounds may be premixed with these fuel compositions prior to distribution or storage. For example, and without limitation, by combining one or more compounds with a bulk fuel in a blending tank or fuel depot. In one or more embodiments, one or more compounds may be added later as a separate additive, depending on a fuel environment or a measured swelling performance of an elastomeric seal exposed to a fuel. For example, and without limitation, one or more compounds may be injected into a fuel stream through an additive injection system downstream of a storage tank or at an aircraft refueling point to allow on-demand dosing based on observed seal shrinkage or compatibility requirements. In one or more embodiments, addition of one or more compounds may serve as a swelling additive to support elastomeric seal performance, especially in fuel compositions that lack sufficient aromatic content. In one or more embodiments, fuels typically have low levels of aromatic hydrocarbons may lead to reduced swelling of nitrile or fluorosilicone elastomers, resulting in seal shrinkage and potential leakage. In one or more embodiments, one or more compounds disclosed herein may include structures according to formula (I) that may provide targeted swelling activity through optimized molecular size, polarity, and solubility, while avoiding a higher soot formation, emissions, and toxicity associated with traditional aromatic compounds including but not limited to benzene, toluene, or xylene. In one or more embodiments, one or more compounds may act as swelling agent that include defined cyclic or polycyclic structures with tailored hydrogen-to-carbon ratios that balance fuel compatibility with seal swell performance and may be introduced at concentrations suitable to maintain a stable seal dimension within a system while minimizing negative impacts on combustion emissions.

Referring now to FIG. 1A, an elastomeric seal 100A is illustrated. In one or more embodiments, elastomeric seal 100A may be ring-shaped, although other variations and shapes may be possible and contemplated. An elastomeric seal 100A may include a first configuration having a first volume before exposure to a composition including one or more compounds according to formula (I) as described herein. In one or more embodiments, an elastomeric seal 100A may include a first dimension 104A across an inner diameter of the ring shape and a second dimension 108A across an outer diameter of the ring shape.

Referring now to FIG. 1B, an elastomeric seal 100B is illustrated. In one or more embodiments, elastomeric seal 100B may be ring-shaped, although other variations and shapes may be possible and contemplated. In one or more embodiments, upon exposure to one or more compounds with formula (I), an elastomeric seal 100A with first dimension 104A may swell, across an inner diameter that is greater than the first dimension 104A to form a third dimension 104B. In one or more embodiments, upon exposure to one or more compounds with formula (I), an elastomeric seal 100A with second dimension 108A may swell, across an outer diameter that is greater than the second dimension 108A to form a fourth dimension 108B. Similarly, an overall volume of elastomeric seal 100A may increase in response to absorption of one or more compounds that result in an expanded volume in elastomeric seal 100B. It should be appreciated that elastomeric seal 100B may also expand into a third spatial dimension that is orthogonal to the view plane of FIGS. 1A-B, such as along an axial thickness of a ring shape, thereby providing three-dimensional expansion of an elastomeric material in response to exposure to one or more compounds.

Figure 2:
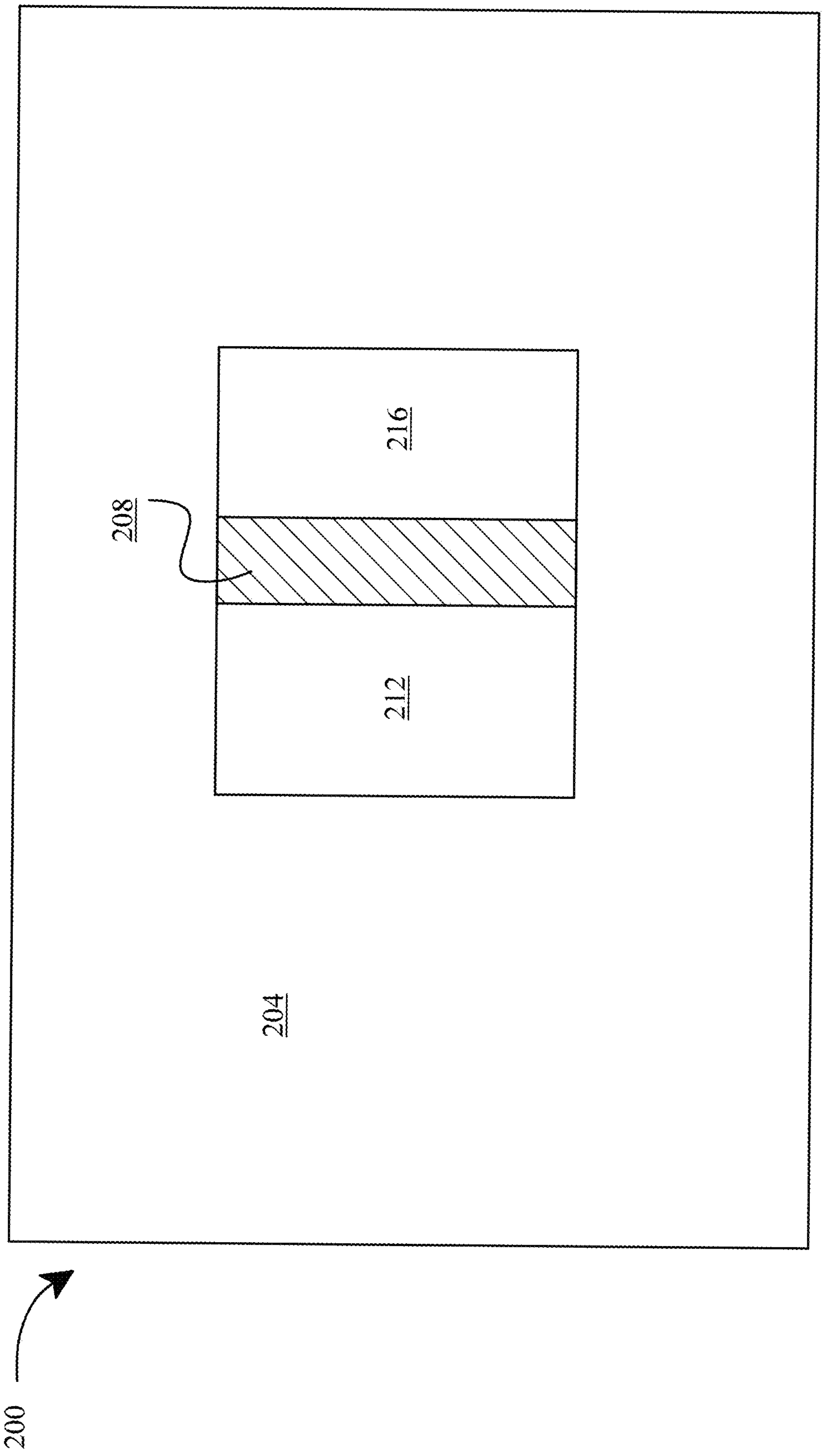
FIG. 2 is an exemplary embodiment of an elastomeric seal in a fuel system.

Referring now to FIG. 2, an exemplary embodiment of an elastomeric seal in a fuel system 200 is illustrated. In one or more embodiments, a fuel system 200 may include an interior space 204. In one or more embodiments, an elastomeric seal 208 may be positioned in an interior space 204 of a fuel system 200 for its intended purpose. In one or more embodiments, a composition including one or more compounds according to formula (I) as described herein may be added to a fuel system 200 in which an elastomeric seal may be located. A "fuel system," as used in this disclosure, is a network of components and assemblies responsible for storing, transferring, metering, and delivering fuel from storage tanks through to a point of use. For example, without limitation, a fuel may include liquid fuel, gaseous fuel. For example, and without limitation, a point of use may include combustion site, engine, or burner located in vehicles, aircraft, industrial equipment, or stationary installation. In one or more embodiments, an elastomeric seal may be positioned in aviation fuel systems, automotive vehicle fuel systems, heavy-duty vehicle fuel systems, marine fuel systems, industrial fuel storage and distribution system, stationary fuel storage and distribution system, refueling and distribution infrastructure. In one or more embodiments, an elastomeric seal may be used as O-rings and gaskets in flanged joints, valve systems and connector fittings. In one or more embodiments, an elastomeric seal may act as pump shaft and housing seals. In one or more embodiments, an elastomeric seal may act as quick-connect/disconnect couplings. In one or more embodiments, an elastomeric seal may act as an inline filter seals. In one or more embodiments, an elastomeric seal may act injector and manifold sealing rings.

With continued reference to FIG. 2, in a fuel system 200, an elastomeric seal may be positioned at an interface of a first component 212 and a second component 216 in order to provide a leak preventing seal between the first component and the second component. In one or more embodiments, an elastomeric seal may be exposed to a fluid provided in a fuel system 200 and such fluid may pass through a first component and a second component. As a result, when a composition including one or more compounds according to formula (I) is provided in a fuel system 200, a composition may come into contact with an elastomeric seal and induce swelling thereof. In one or more embodiments, a swelling of an elastomeric seal may create greater contact between an elastomeric seal and a first component and a second component in order to provide a leak-free engagement therebetween.

Figure 3:
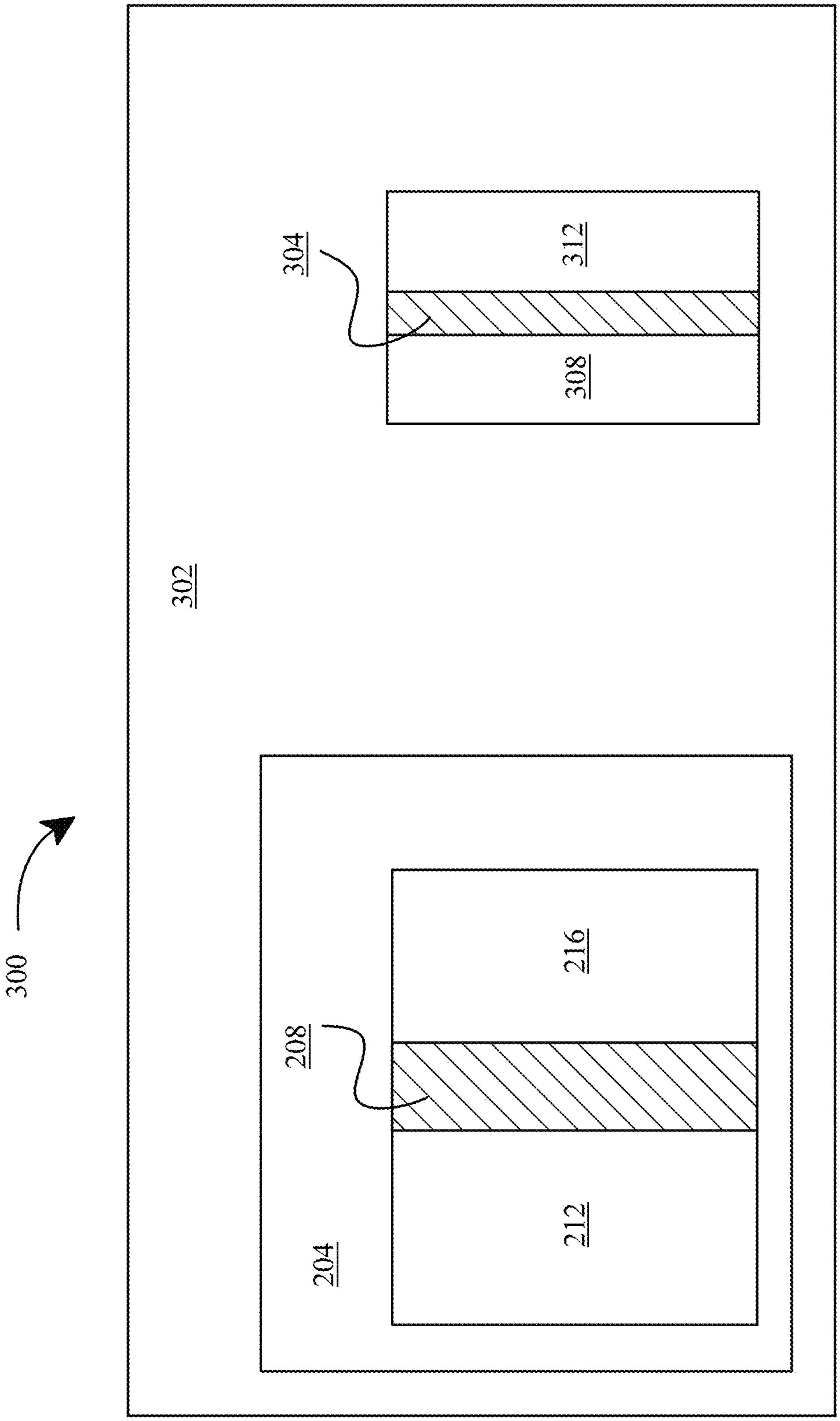
FIG. 3 is an exemplary embodiment of an elastomeric seal in a combustion engine.

Referring now to FIG. 3, an exemplary embodiment of an elastomeric seal in a combustion engine 300 is illustrated. In one or more embodiments, a combustion engine 300 may be an internal combustion engine. For example, and without limitation, internal combustion engines engine may include two-stroke engine, four-stroke engine, gasoline engine, petrol engine, diesel engine, spark-ignition engine, compression-ignition engine, gas turbine engine, rotary engine, rocket engines. In one or more embodiments, combustion engine 300 may include components of fuel system 200 including, an interior space 204 an elastomeric seal 208, a first component 212 and a second component 204. In one or more embodiments, a combustion engine 300 may include an interior space 302 that contains fuel system 200. In one or more embodiments, a combustion engine 300 may include a number of elastomeric seal, one of which elastomeric seal 304. In one or more embodiments, an elastomeric seal 304 may be positioned at an interface of a first combustion engine component 308 and a second combustion engine component 312 in order to provide a leak preventing seal between a first combustion engine component 308 and a second combustion engine component 312.

With continued reference to FIG. 3, in one or more embodiments, an elastomeric seal 304 may be exposed a fluid provided by a fuel system 200 to an internal combustion engine 300 and that passes through a first combustion engine component 308 and a second combustion engine component 312. As such, when a composition including one or more compounds according to formula (I) is provided in a fuel system 200, and in turn to an internal combustion engine 300, it may come into contact with an elastomeric seal 304 and induce swelling thereof. Amongst other possibilities, a swelling of an elastomeric seal 304 may create greater contact between an elastomeric seal 304 and a first combustion engine component 308 and a second combustion engine component 312 in order to provide a leak-free engagement therebetween. Forms in which a composition including one or more compounds according to formula (I) is provided directly to an internal combustion engine 300 without passing through a fuel system 200 may also be possible and contemplated.

In some forms, a composition including one or more compounds according to formula (I) may be mixed with one or more fuel compositions before being added to the fuel system 200 and/or the internal combustion engine 300. These fuel compositions may include synthetic paraffinic kerosene (SPK), Jet-A fuel, hydrogen processed esters and fatty acid compositions known as HEFA or HEFA-Jet, and/or L-Jet, just to provide a few non-limiting examples. Alternatively, in some forms, a composition including one or more compounds according to formula (I) may be added to the fuel system 200 and/or the internal combustion engine 300 as a separate seal-swelling additive.

In some forms, the compositions described herein may be entirely or substantially free of any petroleum-based or petroleum-derived compounds, although forms in which petroleum-based or petroleum-derived compounds are present are contemplated and possible. In some forms, the compositions described herein may be entirely or substantially free of any aromatic compounds, although forms in which aromatic compounds are present are contemplated and possible.

Figure 4:
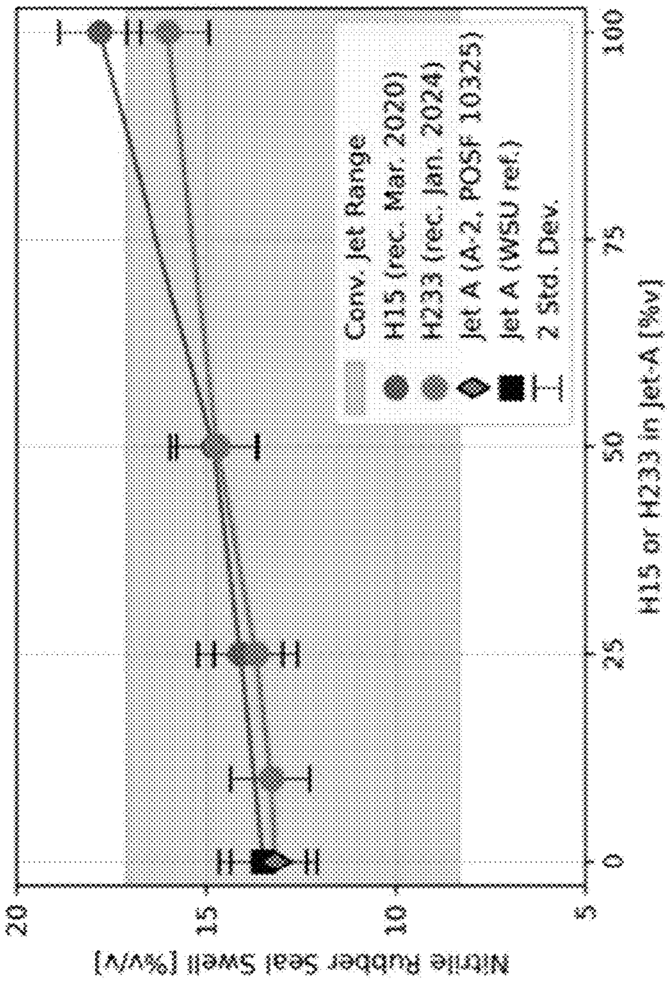
FIG. 4 is a graphical illustration of seal swelling effectiveness results for various compositions.

Referring now to FIG. 4, graphical illustration of seal swelling effectiveness results for various compositions is illustrated. Different compositions including one or more compounds according to formula (I) as described herein were tested to determine their effectiveness in promoting swelling of nitrile rubber seals. More specifically, the effectiveness of DMCO-based compositions, referred to as H15 and H233, for swelling nitrile rubber seals was evaluated. These H15 and H233 compositions were tested at various concentrations, either blended with Jet-A fuel or used on their own and then compared with the performance of Jet-A alone as well as with the typical seal swelling effectiveness range of conventional jet fuel. The x-axis shows the concentration of H15 or H233 in Jet-A fuel, expressed in volume percent (% v/v), ranging from 0% to 100%. The y-axis shows the amount of nitrile rubber seal swell, measured as percent volume change (% v/v), which indicates how much the nitrile rubber expanded due to fuel exposure. The shaded green area in FIG. 4 marks the range of seal swelling typically observed with conventional jet fuels, which serves as a reference to judging acceptable performance. As the concentration of H15 or H233 increases, the seal swelling generally increases. At 100% concentration, the H15 composition exceeded the upper limit of the conventional seal swelling range, while the H233 composition remained near the higher end of that range. These results indicate that increasing the concentration of H15 or H233 can enhance seal swelling, but care may be needed to avoid excessive swelling beyond conventional fuel performance.

Figure 5:
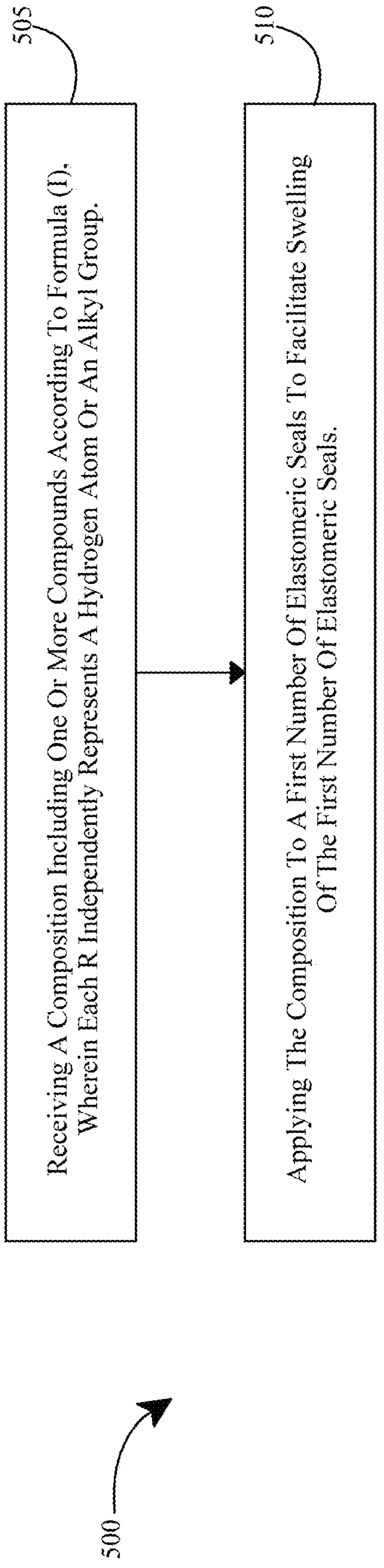
FIG. 5 a flow diagram of an exemplary method for use of seal swelling compositions.

Referring now to FIG. 5, a flow diagram of an exemplary method 500 for use of seal swelling compositions. At step 505, method 500 includes receiving a composition including one or more compounds according to formula (I), wherein each R independently represents a hydrogen atom or an alkyl group. This may be implemented as described and with reference to FIGS. 1-4.

With continued reference to FIG. 5, method 500 includes a step 510. At step 510, method 500 includes applying the composition to a first number of elastomeric seals to facilitate swelling of the first number of elastomeric seals. This may be implemented as described and with reference to FIGS. 1-4.

Figure 6:
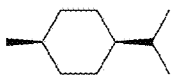
FIG. 6 is an exemplary embodiments of various hydrogenated isoprene dimers.
Figure 6:
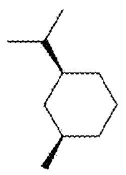
Figure 6:
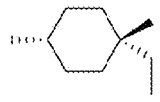
Figure 6:
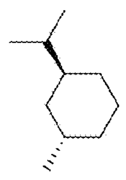
Figure 6:
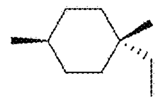
Figure 6:
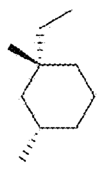
Figure 6:
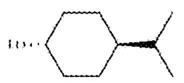
Figure 6:
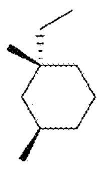

Referring now to FIG. 6, an exemplary embodiments of various hydrogenated isoprene dimers (HIDs) is illustrated. In one or more embodiment, HIDs may include (1s,4s)-1-isopropyl-4-methylcyclohexane, (1s,4s)-1-ethyl-1,4-dimethylcyclohexane, (1S,3R)-1-isopropyl-3-methylcyclohexane, (1S,3S)-1-isopropyl-3-methylcyclohexane, (1r,4r)-1-ethyl-1,4-dimethylcyclohexane, (1r,4r)-1-isopropyl-4-methylcyclohexane, (1R,3S)-1-ethyl-1,3-dimethylcyclohexane, (1R,3R)-1-ethyl-1,3-dimethylcyclohexane.

EXAMPLES

The following examples are intended to be illustrative of the disclosure only and are not intended to limit the scope or underlying principles in any way.

Different compositions including one or more compounds according to formula (I) as described herein were tested for effectiveness to provide swelling of nitrile rubber seals. More specifically, effectiveness for DMCO compositions referred to as H15 and H233 for swelling a nitrile rubber seal was tested. The H15 and H233 compositions were tested at different concentrations in an admixture with Jet-A or alone relative to the effectiveness of Jet-A alone and the seal swelling effectiveness range of conventional jet fuel. The different compositions were tested in a manner similar to that set forth in Section 2.2 of "Measurements of Nitrile Rubber Absorption of Hydrocarbons: Trends for Sustainable Aviation Fuel Compatibility" by Faulhaber et al., *Bioenergy, Biofuels, and Biorefinery*, Jun. 7, 2023. The results of the testing are graphically illustrated in FIG. 4 which shows, amongst other things, that seal swelling effectiveness increased as the concentration of the H15 and H233 compositions increased. In addition, at 100% concentration, the H15 composition exceeded the seal swelling effectiveness range of conventional jet fuel and the seal swelling effectiveness of the H233 composition was near the upper end of the seal swelling effectiveness range of conventional jet fuel.

What is claimed is:

1. A method for use of seal swelling compositions comprising:

receiving a composition including one or more compounds according to formula (I), wherein each R independently represents a hydrogen atom or an alkyl group

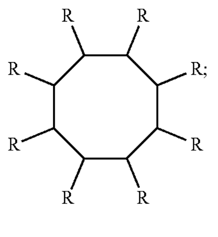

(I)

and applying the composition to a first number of elastomeric seals to facilitate swelling of the first number of elastomeric seals.

2. The method of claim 1, wherein the first number of elastomeric seals are positioned in a fuel system.

3. The method of claim 1, wherein the composition is mixed with one or more fuel compositions selected from the group consisting of synthetic paraffinic kerosene (SPK), Jet-A fuel, HEFA, HEFA-Jet and L-Jet.

4. The method of claim 2, wherein the fuel system is a component of an internal combustion engine including a second number of elastomeric seals.

5. The method of claim 4, further comprising injecting the composition into the internal combustion engine to facilitate swelling of the second number of elastomeric seals.

6. The method of claim 1, wherein the one or more compounds according to formula (I) comprise one or more of a following compounds:

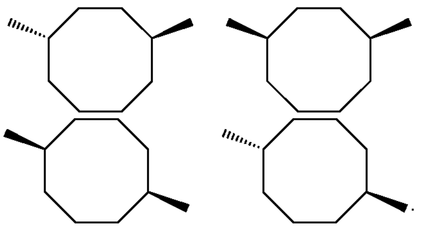

7. The method of claim 1, wherein the composition further comprises one or more compounds having one of following structures:

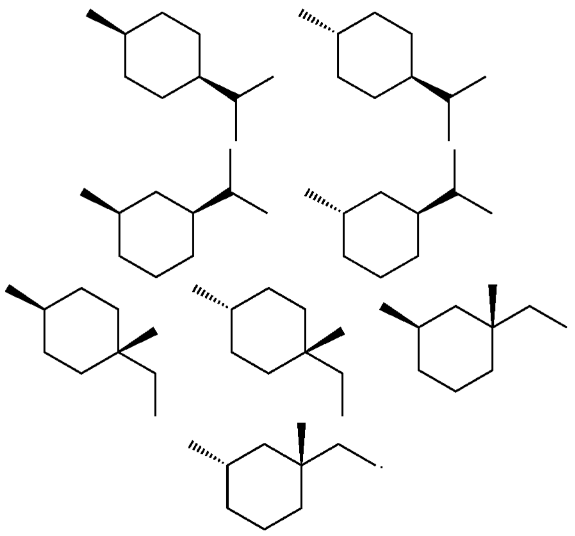

8. The method of claim 1, wherein the composition is free of aromatic compounds.

9. The method of claim 1, wherein the composition is free of petroleum-based compounds.

10. The method of claim 1, wherein the composition comprises one or more petroleum-based compounds.

11. The method of claim 1, wherein the composition comprises between about 1% and about 100% by weight of the one or more compounds according to formula (I).

12. The method of claim 1, wherein the composition comprises between about 50% to and about 99% by weight of the one or more compounds according to formula (I).

13. An elastomeric seal, comprising a body configured to expand from a first configuration having a first volume to a second configuration having a second volume larger than the first volume in response to exposure to a composition including one or more compounds according to formula (I)

(I)

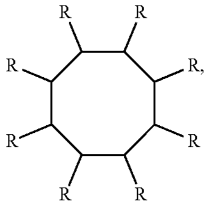

wherein each R independently represents a hydrogen atom or an alkyl group.

14. The elastomeric seal of claim 13, wherein the one or more compounds according to formula (I) comprise one or more of a following compounds:

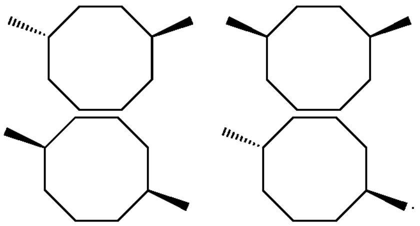

15. The elastomeric seal of claim 13, wherein the composition further comprises one or more compounds having one of following structures:

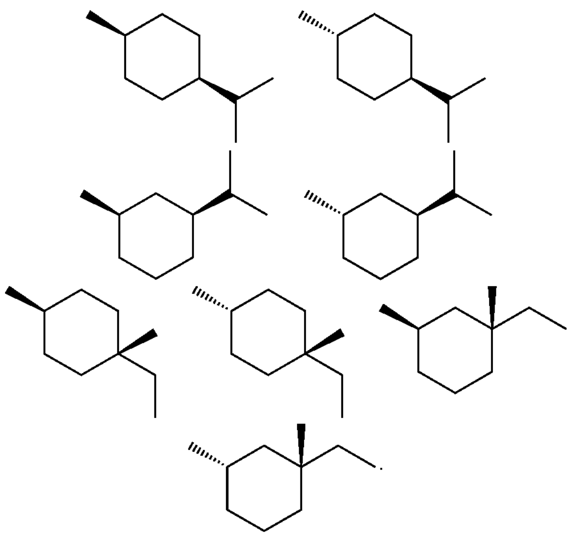

16. The elastomeric seal of claim 13, wherein the composition is free of aromatic compounds.

17. The elastomeric seal of claim 13, wherein the composition is free of petroleum-based compounds.

18. The elastomeric seal of claim 13, wherein the composition comprises one or more petroleum-based compounds.

19. The elastomeric seal of claim 13, wherein the composition is positioned in a fuel system.

20. The elastomeric seal of claim 19, wherein the fuel system is a component of an internal combustion engine.

* * * * *